United States Patent [19]
Lafon

[11] 3,939,260
[45] Feb. 17, 1976

[54] THERAPEUTIC AND COSMETIC COMPOSITIONS
[75] Inventor: Victor Lafon, Paris, France
[73] Assignee: Societe Anonyme dite: Orsymonde, Paris, France
[22] Filed: Oct. 7, 1974
[21] Appl. No.: 512,926

Related U.S. Application Data
[63] Continuation of Ser. No. 92,862, Nov. 25, 1970.

[30] Foreign Application Priority Data
Nov. 26, 1969 France............................ 69.40803
Mar. 24, 1970 France............................ 70.10548

[52] U.S. Cl. ........................ 424/28; 34/5; 34/12; 34/19; 252/91
[51] Int. Cl.[2]. A61K 9/10; A45D 40/00; A61K 7/48
[58] Field of Search .......... 252/91; 260/2.5; 424/28; 15/506, 209, 244; 34/5, 12, 19

[56] References Cited
UNITED STATES PATENTS

| | | | |
|---|---|---|---|
| 259,268 | 6/1882 | Buczkowski | 424/28 X |
| 1,687,643 | 10/1928 | Berliner | 424/28 X |
| 1,836,833 | 12/1931 | Ames | 424/28 X |
| 2,034,697 | 3/1936 | Factor | 424/63 |
| 2,101,843 | 12/1937 | Factor et al. | 424/63 |
| 2,617,754 | 11/1952 | Neely | 424/63 |
| 2,999,265 | 9/1961 | Duane et al. | 15/506 |
| 3,002,937 | 10/1961 | Parker et al. | 260/2.5 |
| 3,094,735 | 6/1963 | Hanlon | 15/506 |
| 3,283,357 | 11/1966 | Decker et al. | 15/506 |
| 3,470,883 | 10/1969 | Shepherd et al. | 131/10 |

OTHER PUBLICATIONS 4.23.74 Translation U.S. Pat. Off. of Spanish Language Article by Schmidt Walters, Anales 19:115–119 (1968) "Study of the Lyophilization of Oil/Water Emulsions Part II" 5 pp., abst. 70 No. 71277b (Apr. 21, 1969). in Chem. abst. 70
Remington's Practice of Pharmacy, 12th Ed. 1961 pp. 155, 156, 338.

Primary Examiner—Shep K. Rose

[57] ABSTRACT

Lyophilised oil-in-water emulsions and suspensions are useful as compositions for dermatological, cosmetological, buccal, and dental use having the advantage over conventional compositions of lower bulk and better storage stability.

2 Claims, No Drawings

THERAPEUTIC AND COSMETIC COMPOSITIONS

This is a continuation of application Ser. No. 92,862 filed Nov. 25, 1970.

The present invention relates to compositions for dermatological or cosmetic use, and more particularly, to compositions for the hygiene and protection of the skin, the teeth and the scalp.

In dermatology, acitve principles intended for external treatments of the skin and teguments are very frequently combined with a fatty excipient to give unguents, cerates, plasters or ointments.

The development of modern excipients has made it possible in many cases, both in dermatology and in cosmetology, to replace these fatty preparations, which stain and are not well absorbed by the skin, by creams of the oil-in-water emulsion type, which are valued because of their properties of being washable, of giving, after rubbing in, an invisible non-fatty film, and of penetrating easily into the skin.

However, the field of application of these creams is limited to biologically active substances which are stable in the presence of water, which excludes a large number of biologically active material, including many enzymes, antibiotics, organ extracts, hormones and the like, and combinations of biologically active materials which are incompatible in the presence of water.

Even with stable ingredients, aqueous creams can present certain disadvantages to the user, such as: the need to cary a bulky tube or pot if the material is to be applied several times daily, or is to be taken on a journey; and poor dosing of the active principles because the amount of cream applied by rubbing can vary greatly each time some is taken, depending on whether it is taken from a tube or from a pot.

These disadvantages, which restrict the field of application of the creams, can be remedied by the present invention, which provides a composition produced by lyophilisation of an oil-in-water emulsion comprising:

a. an active principle as hereinafter defined:

b. a fatty acid, fatty acid derivative, fatty alcohol, fatty alcohol derivative, animal, vegetable or mineral fatty substance, or a synthetic fatty substance which is solid at normal temperature and pressure but melts at moderately elevated temperature; and c. a solution in water of a thickener and an emulsifier. Such compositions can be added to water to give at the time of use an aqueous solution for dermatological or cosmetological use, such as a cream, lotion, milk or jelly, in which the active principle or principles are entirely preserved regardless of their stability in water.

Apart from questions of stability, the new compositions also provide greater ease of use, in out-patient treatment, of all the active materials which can be used in dermatology and in cosmetology, and allows them to be applied at well-defined unit doses.

The new compositions can optionally also contain customary ingredients, for example perfumes, dyestuffs, buffers and preservatives.

The lyophilised product is a solid, dry, spongy, non-hygroscopic but rather hydrophilic mass which gives, after brief immersion in water and as a result of rubbing onto the skin, a cream, jelly, milk or lotion for dermatological or cosmetological use.

The compositions can be in unit doses and may be in the form of extremely diverse shapes and sizes, e.g. parallelepipeds, cylinders, spheres, hemispheres, truncated cones and the like.

The term "active principle" as used herein includes both medicines for external use and cosmetic products for the hygiene and protection of the skin, the mouth, the teeth and the hair, such as, for example, emollients, detergents, depilatories, deodorisers, soothing pastes, anti-sunburn compositions, anti-perspiration compositions, anti-dandruff compositions and antiseptics. The active principle may be, for example, a corticosteroid, phenylbutazone, an antibiotic, an enzyme, a vitamin, or a vegetable or animal extract.

The lipid phase of the new compositions may contain at least one, and preferably several, of the following substances: fatty acids and their derivatives (salts and esters); fatty alcohols and their derivatives (esters); and complex fatty substances of animal, vegetable or synthetic origin, for example lanolins, paraffins, spermaceti, animal waxes, vegetable waxes and synthetic waxes.

The hydrophilic phase may contain as thickeners, for example, one of the following: natural gums (gum arabic, gum tragacanth and guar gum); cellulose derivatives; pectins (including derivatives of alginic acid and of carragheen); bentonites and colloidal silicas; polysaccharides; synthetic macromolecules (with vinyl or acrylic groups or the like); starchy materials; phosphorylated derivatives of aliphatic hydroxylic alcohols; and natural or semi-synthetic inter-esterified triglycerides.

As emulsifiers, the hydrophilic phase may contain: surface-active agents, which may be non-ionic, for example Tweens, Spans and the like; anionic, for example lauryl sulphates, or cationic, for example quaternary ammonium compounds; and dispersing agents, such as organic polyelectrolytes, e.g. derivatives of alkylarylsulphonic acid, and organic or inorganic salts of stearic acid, and oxyethyleneated fatty alcohols.

One or more of each of these materials can be used, in varying amounts.

The new compositions are prepared essentially by lyophilising an aqueous emulsion of ingredients chosen to form the said compositions, in lyophilisation tanks comprising a series of cells of suitable size and shape.

More particularly, a cream, lotion, milk or jelly may be prepared as follows: All the constituents of the lipid phase and, if desired, all the active products or products which are insoluble in this phase, are mixed, and the phase is melted by heating and homogenised. Further, the hydrophilic phase consisting of a more or less fluid jelly consisting of the thickeners, the emulsifiers and, if desired, other compounds which are soluble or insoluble in water, is prepared. The hot oily phase is then poured into the aqueous phase which has been heated to the same temperature, so as to yield, on stirring, a perfect emulsion, which can either be poured hot into cells having the desired shape and size for the desired unit dose, or be cooled in bulk so that any active principle or principles which are too labile to withstand an increase in temperature in the aqueous phase can be incorporated into the material immediately before distribution into the cells. The cells, containing the cooled preparation, are then frozen so that the temperature of the preparation is lowered approximately to between $-18°$ and $-40°C$. It is subjected to freeze-drying or lyophilisation under a high vacuum at about $10^{-2}$mm Hg, in such a way that the heat required for the sublimation of the water is supplied while the temperature does not rise to above the freezing point of the product.

The invention thus makes it possible to improve the physical characteristics, especially the consistency and the structure, of compositions for dermatological or cosmetological use, by combining the active principle or principles with the excipients quoted above.

Finally, the freezing conditions can be modified so as to vary the structure of the mass by changing the size of the crystals. For example, the freezing can be carried out on vibrating plates, moved by electromagnetic vibrations or ultrasonics.

After lyophilisation, the compositions obtained can be packaged in different ways: Either in bulk, in boxes or tubes, or in unit sachets, or, finally, in a preferred presentation intended to facilitate their use, as described below.

After immersion in water, the particles of lyophilised product rapidly become soft and difficult to handle. To avoid this disadvantage, the particles of lyophilised product may be placed on a wide-mesh fabric screen which can neither resist the passage of water nor the passage of the reconstituted emulsion for application to the skin. This screen can consist of natural or synthetic fibres. It is advantageous to use heat-weldable fabrics, the use of which presents convenient features for industrial presentation.

The particles of lyophilised product contained in their individual sachet of permeable fabric can be protected in a sachet of paper or aluminium, by themselves or combined with a plastic film (for example of polyethylene). The sachets thus obtained can be packaged in varying numbers in cardboard containers or in another packaging material.

Presentation inside a natural or synthetic sponge is different from that of the textile sachet. Preferably, a synthetic sponge, such as polyurethane foam, is used. The foam is dipped into the liquid emulsion and becomes impregnated through compression followed by expansion in situ. The whole, consisting of the composition and the supporting foam, is lyophilised, the amount of emulsion absorbed being a function of the diameter and number of the pores and of the viscosity of the composition.

The invention makes it possible to produce compositions which are stable over a period of time or which contain molecules or substances which are unstable or incompatible in the presence of water. Suitable unstable substances include products of natural origin possessing a physiological activity which is dependent on the material not having deteriorated, and which is not preserved well over a period of time. Products of natural origin which can be used as they are or combined with stabilisers, and which are suitable, include especially: (a) mineral products, namely spa muds and spa waters, oyster-bed muds, vegeto-mineral muds, waters containing sulphur, sodium, calcium or magnesium, waters rich in trace elements, expecially trace metal elements, waters containing iodine and bromine, and waters producing nascent sulphur; and (b) products of animal or vegetable origin, such as spa plankton, marine plankton, fish milt, algae and marine plants, shellfish, oysters and fish. These various products can be taken directly from their natural location and used as such, after dehydration by lyophilisation; they can, if desired, be combined with stabilisers. They can also be cultured or enriched in media, the composition of which can be modified to increase the content of certain natural constituents, such as sulphur, iodine, trace elements, vitamins, aminoacids and radioactive products, to the desired extent.

The majority of shampoos and compositions for use on the hair, or for treatment of the scalp, are in a liquid form which suffers from the same disadvantages as those mentioned above for cosmetic and dermatological compositions. The present invention makes it possible to produce lyophilised compositions useful as shampoos and for the treatment of the scalp containing physiologically active, unstable products.

In compositions intended for buccal or dental hygiene, the importance of the lipid phase combined with the hydrophilic phase and with the active substances is less, and the lipid phase can in certain cases be absent. On the other hand, the buccal or dental compositions generally contain a greater or lesser content of insoluble materials intended to clean and polish the teeth, e.g. cleaning agents of natural origin, such as calcium carbonate, calcium phosphate, silica, mangesia and sodium polymetaphosphate or of synthetic origin, such as polyethylene, silicone, chlorofluorinated resin and cellulose acetate, these polymers being used in powder form. Other constituents, such as emulsifiers, thickeners, foaming agents, perfumes, buffers, preservatives and dyestuffs can also be incorporated as indicated below.

The Examples which follow illustrate the invention.

Examples 1 to 4 relate to compositions for cosmetological use.

Examples 5 to 19 relate to compositions for dermatological use.

Examples 5 to 9 relate to active principles which are stable in the aqueous phase, but which can be more easily used as a result of the invention.

Examples 9 to 19 relate especially to active principles which are unstable or incompatible in the aqueous phase.

Examples 20 to 23 relate to dentifrice pastes.

Examples 24 to 27 relate to compositions for treatment of the hair or scalp.

Example 28 relates to a preferred form of cream for external use.

EXAMPLE 1

| Emollient Cleansing Cream | | |
|---|---|---|
| Lipid phase | | |
| Ethoxylated lanolin | | 1 g. |
| Stearyl alcohol | | 3 g. |
| Cetyl alcohol | | 3 g. |
| Sodium lauryl sulphate | | 1 g. |
| Palm oil sucroglyceride | | 1 g. |
| Aqueous phase | | |
| High viscosity carboxymethylcellulose | | 0.1 g. |
| Lithium, sodium and magnesium triple fluosilicate | | 2.5 g. |
| Methyl para-hydroxybenzoate | | 0.1 g. |
| Rose water | | 20 g. |
| Phosphoric acid | q.s.p. pH 5 | |
| Purified water | q.s.p. | 100 g. |

Method of Preparation

1. The ethoxylated lanolin, the stearyl and cetyl alcohols and the palm oil sucroglyceride are melted together. The sodium lauryl sulphate is added and the mixture is heated to about 75°C.

2. Further, the high viscosity carboxymethylcellulose is swollen in the rose water until a translucent homogeneous gel is obtained.

3. The methyl para-hydroxybenzoate is dissolved hot in the total amount of purified water. The lithium, sodium and magnesium triple fluosilicate is added to this solution, with vigorous stirring. After half an hour, a homogeneous dispersion is obtained, to which phosphoric acid is added to adjust the pH to about 5.

4. The carboxymethylcellulose gel prepared under 2) and the lithium, sodium and magnesium triple fluosilicate dispersion prepared under 3) are mixed. The mixture is heated to 70°C.

5. The hot aqueous phase obtained under 4) is poured into the oily phase prepared under 1), while the latter is stirred.

6. An emulsion of the oil-in-water type is obtained which, after cooling, gives a cream.

7. This cream is distributed in cylindrical cells of diameter about 15 mm and depth about 10 mm, which each contain about 2 g. of cream.

8. All the cells are cooled in the cold chamber of a lyophilisation apparatus to a temperature of −35°C, after some hours. The cooling is then stopped. A vacuum is applied, and the heating of the plates of the apparatus, on which the cells have been placed, is begun. The temperature of the cells remains at between −10° and −25°C for several hours, while the temperature of the plates is raised from −40° to +5°C to +10°C. The vacuum used during the process is about $10^{-2}$ mm Hg.

The lyophilisation process is allowed to continue for at least 12 hours, and the plates are then heated to +20°C. When the temperature of the cells has reached equilibrium with that of the plates near 20°C, the lyophilisation can be considered complete. The vacuum in the apparatus is then released. The lyophilised masses are removed from the cells; they are placed on a strip of "Tergal" gauze and then covered with a strip of the same quality. The two strips of Tergal are sealed round the lyophilised masses, using an apparatus with resistance heaters, so that after cutting off, square sachets of 2 cm side length are obtained. These sachets are then placed beneath a polyethylene film, which is then heat-sealed.

In the examples which follow, the procedure of Example 1 is adopted to prepare the compositions described.

EXAMPLE 2

Deodorising and Anti-Perspiration Cream

Lipid phase

| | | |
|---|---|---|
| Stearic acid | 6 | g. |
| Beeswax | 1 | g. |
| Polyoxyethylene stearate | 2 | g. |
| Polyoxyethylene and polyoxypropylene Stearate | 2 | g. |
| Lavender essence | 0.25 | g. |
| Hexachlorophene | 0.5 | g. |

Aqueous phase

| | | | |
|---|---|---|---|
| Aluminogluconic acid | | 10 | g. |
| Hydroxyethylcellulose | | 0.25 | g. |
| Aluminium-magnesium double silicate | | 3 | g. |
| Distilled water | q.s.p. | 100 | g. |

EXAMPLE 3

Cream to Prevent Sunburn

Lipid phase

| | | |
|---|---|---|
| Ethyl p-dimethylaminobenzoate | 2 | g. |
| Stearyl alcohol | 4 | g. |
| Stearic acid | 1 | g. |
| Sodium lauryl sulphate | 1 | g. |
| Coumarin | 0.10 | g. |
| Titanium oxide | 0.5 | g. |
| Neocolamin | 0.5 | g. |
| Yellow Iron oxide | 0.05 | g. |

Aqueous phase

| | | | |
|---|---|---|---|
| Propyl para-hydroxybenzoate | | 0.05 | g. |
| Starch | | 10 | g. |
| Colloidal silica | | 5 | g. |
| Aluminium-magnesium double silicate | | 2 | g. |
| Phosphoric acid | q.s.p.pH | 7 | |
| Distilled water | q.s.p. | 100 | g. |

In this example, the starch replaces the cellulose derivative used in Example 1.

EXAMPLE 4

Hand Cream

Lipid phase

| | | |
|---|---|---|
| Glycerol monostearate | 4 | g. |
| Lanolin alcohols | 3 | g. |
| Stearic acid | 1.5 | g. |
| Boric acid | 2 | g. |

Aqueous phase

| | | | |
|---|---|---|---|
| Methylcellulose | | 0.3 | g. |
| Polyethyleneglycol 4000 | | 4 | g. |
| Lithium, sodium and magnesium triple fluosilicate | | 3 | g. |
| Lilly of the Valley essence | | 0.01 | g. |
| Distilled water | q.s.p. | 100 | g. |

EXAMPLE 5

Protective Cream for Dermatological Use

Lipid phase

| | | |
|---|---|---|
| Magnesium silicate | 10 | g. |
| Zinc oxide | 10 | g. |
| Polyglycol ether of saturated Fatty alcohols | 5 | g. |
| Cetyl alcohol | 5 | g. |
| Stearyl alcohol | 5 | g. |
| Polyoxyethylene-sorbitane monostearate | 1.5 | g. |
| Sorbitan monostearate | 1 | g. |

Aqueous phase

| | | | |
|---|---|---|---|
| Polyvinylpyrrolidone | | 2 | g. |
| Lithium, magnesium and sodium triple fluosilicate | | 3 | g. |
| Citric acid | q.s.p. pH | 5.5 | |
| Distilled water | q.s.p. | 100 | g. |

EXAMPLE 6

Anti-Inflammation Cream Based on Corticosteroid

Lipid phase

| | | |
|---|---|---|
| Delta-hydrocortisone | 0.5 | g. |
| Cetyl alcohol | 3 | g. |
| Stearyl alcohol | 3 | g. |
| Sodium Lauryl sulphate | 1 | g. |

Aqueous phase

| | | | |
|---|---|---|---|
| Polyethyleneglycol 4000 | | 2 | g. |
| Lithium, magnesium and sodium triple fluosilicate | | 2.5 | g. |
| Carboxyvinyl polymer | | 0.2 | g. |
| Phosphoric acid | q.s.p.pH6 | | |
| Distilled water | q.s.p. | 100 | g. |

In this example, the binder consists of a "CARBOPOL" carboxyvinyl polymer dispersed in water and then mixed with the gel of lithium, magnesium and sodium fluosilicate to form the base of the aqueous phase.

EXAMPLE 7

Antiseptic Cream

Lipid phase

| | | |
|---|---|---|
| Thymol | 1 | g. |
| Salol | 1.5 | g. |
| Menthol | 0.5 | g. |
| Cetyl alcohol | 10 | g. |
| Sodium lauryl sulphate | 1 | g. |

Aqueous phase

| | | |
|---|---|---|
| Polyethyleneglycol 6000 | 2 | g. |
| Ethylhydroxyethylcellulose | 0.2 | g. |
| Microcrystalline cellulose | 0.1 | g. |
| Aluminium-magnesium double silicate | 2 | g. |
| Lactic acid | q.s.p.pH5 | |
| Distilled water | q.s.p. 100 | g. |

EXAMPLE 8

Anti-Inflammation Cream

Lipid phase

| | | |
|---|---|---|
| Inter-esterified hydrogenated palm oil | 5 | g. |
| Oxyethylenated fatty alcohols | 5 | g. |

Aqueous phase

| | | |
|---|---|---|
| Carboxymethylcellulose H.V. | 0.2 | g. |
| Lithium, magnesium and sodium trifluosilicate | 2.5 | g. |
| Disodium phosphate | q.s.p.pH8 | |
| Distilled water | q.s.p. 100 | g. |
| Dextran sulphate | 2 | g. |
| Sodium salt of phenylbutazone | .4 | g. |

The method of preparation is as in Example 1; the active principles are added to the cooled cream.

EXAMPLE 9

Cream containing an Antibiotic and a Soluble Steroid

Lipid phase

| | | |
|---|---|---|
| Cetyl alcohol | 5 | g. |
| Stearyl alcohol | 5 | g. |
| Sodium dioctylsulphosuccinate | 1.5 | g. |
| Polyoxyethylene lauryl ether | 3 | g. |
| Ethylene oxide ether of lanolin alcohols | 2 | g. |

Aqueous phase

| | | |
|---|---|---|
| Methyl para-hydroxybenzoate | 0.1 | g. |
| Carboxymethylcellulose B.V. | 0.2 | g. |
| Aluminium-magnesium double silicate | 2.5 | g. |
| Disodium phosphate | q.s.p.pH7 | |
| Distilled water | q.s.p. 100 | g. |
| Sodium-chloroamphenicol monosuccinate | 0.15 | g. |
| Beta-methasone phosphate | 0.10 | g. |

The excipient is prepared in accordance with the general process described in Example 1. The chloramphenicol salt and the beta-methasone salt are added to the cream obtained by cooling the emulsion, before distribution into cells.

EXAMPLE 10

Cream Combining Two Active Principles which are Incompatible in the Aqueous Phase Lipid Phase

| | | |
|---|---|---|
| Cetyl alcohol | 4 | g. |
| Stearyl alcohol | 4 | g. |
| Sodium lauryl sulphate | 1 | g. |

Aqueous phase

| | | |
|---|---|---|
| Lithium, magnesium and sodium triple fluosilicate | 2.5 | g. |
| Carboxymethylcellulose B.V. | 0.15 | g. |
| Polyethyleneglycol 4000 | 1 | g. |
| Phosphoric acid | q.s.p.pH7 | |
| Methyl para-hydroxybenzoate | 0.1 | g. |
| Distilled water | q.s.p. 100 | g. |
| Hyaluronidase | 15,000 | U. |
| Heparinoid substance | 5,000 | U. |

The preparation is carried out in accordance with the process quoted in Example 1; the hyaluronidase and the heparinoid substance are added to the cooled cream just before distribution into cells.

Examples 11 to 13 are prepared by the process of Example 1 using the basic formula quoted in Example 10, and the active ingredients noted below.

EXAMPLE 11

| | | |
|---|---|---|
| Hyaluronidase | 15,000 | U. |
| Desoxymethasone | 0.25 | g. |

EXAMPLE 12

| | | |
|---|---|---|
| Hyaluronidase | 15,000 | U. |
| Tetracycline | 2 | g. |
| Neutral sodium sulphite | 0.1 | g. |

EXAMPLE 13

| | | |
|---|---|---|
| Alpha-mucase | 1,500,000 | U. |
| Hydrocortisone | 0.5 | g. |

The active principles in each of these Examples are added to the cooled cream immediately before its distribution into cells.

EXAMPLE 14

Lipid phase

| | | |
|---|---|---|
| Glycerol monostearate | 2 | g. |
| Cetyl alcohol | 2 | g. |
| Stearyl alcohol | 2 | g. |
| Sodium lauryl sulphate | 1 | g. |

Aqueous phase

| | | |
|---|---|---|
| Aluminium-magnesium double silicate | 3 | g. |
| Propyl para-hydroxybenzoate | 0.05 | g. |
| Sodium alginate | 0.2 | g. |
| Polyethyleneglycol 6000 | 2 | g. |
| Disodium phosphate | 0.5 | g. |
| Phosphoric acid | q.s.p.pH7.5 | |
| Distilled water | q.s.p. 100 | g. |
| Alpha-chymotrypsin | 0.1 | g. |

After preparing the base excipient, as described for Example 1, the alpha-chymotrypsin is added before distributing the material into cells.

In Examples 15 and 16, the following active principles are added to the basic formulation of Example 14:

EXAMPLE 15

| | | |
|---|---|---|
| Heparinoid substance | 5,000 | U. |
| Hyaluronidase | 15,000 | U. |

EXAMPLE 16

| | | |
|---|---|---|
| Heparinoid substance | 5,000 | U. |
| Hyaluronidase | 15,000 | U. |
| Triamcinolone acetonide | 0.1 | g. |

EXAMPLE 17

Cream containing a soluble stabilised penicillin salt

Lipid phase

| | | |
|---|---|---|
| Spermaceti | 7.5 | g. |
| Sodium lauryl sulphate | .1 | g. |

Aqueous phase

| | | | |
|---|---|---|---|
| Lithium, magnesium, sodium triple fluosilicate | | 3 | g. |
| Carboxymethylcellulose B.V. | | 0.2 | g. |
| Polyethyleneglycol 4000 | | 1 | g. |
| Monosodium phosphate | | 0.1 | g. |
| Disodium phosphate | | 0.5 | g. |
| Phosphoric acid | q.s.p.pH7.5 | | |
| Sodium tetracemate | | 0.2 | g. |
| Hexamine | | 1 | g. |
| Distilled water | q.s.p. | 100 | g. |
| Sodium salt of penicillin | | 1,000,000 | I.U. |

EXAMPLE 18

Cream containing a soluble stabilised aureomycin salt

Lipid phase

| | | |
|---|---|---|
| Stearyl alcohol | 7.5 | g. |
| Sodium lauryl sulphate | 1 | g. |

Aqueous phase

| | | | |
|---|---|---|---|
| Aluminium-magnesium double silicate | | 3 | g. |
| Ethylhydroxyethylcellulose | | 0.2 | g. |
| Sodium borate | | 2 | g. |
| Polyethyleneglycol 4000 | | 2 | g. |
| Neutral sodium sulphite | | 0.2 | g. |
| Phosphoric acid | q.s.p.pH6.8 | | |
| Distilled water | q.s.p. | 100 | g. |
| Aureomycin hydrochloride | | 2 | g. |

The aqueous gel obtained by the process described in Example 1 is prepared with part of the distilled water, and the remainder is used to make up a primary solution with the aureomycin hydrochloride, sodium borate and the sodium sulphite. This solution is added to the cooled emulsion of the oily phase in the aqueous phase.

EXAMPLE 19

Vitamin-containing cream with embryo extract

Lipid phase

| | | | |
|---|---|---|---|
| Vitamin A | | 1,000,000 | I.U. |
| Vitamin F | | 2 | g. |
| Butylhydroxyanisole | | 0.1 | g. |
| Propyl gallate | | 0.1 | g. |
| Cetyl alcohol | | 7.5 | g. |
| Sodium lauryl sulphate | | 1 | g. |

Aqueous phase

| | | | |
|---|---|---|---|
| Lithium, magnesium and sodium triple fluosilicate | | 3 | g. |
| Carboxymethylcellulose B.V. | | 0.2 | g. |
| Polyethylene glycol 4000 | | 1 | g. |
| Citric acid | q.s.p.pH5 | | |
| Methyl para-hydroxybenzoate | | 0.1 | g. |
| Propyl para-hydroxybenzoate | | 0.05 | g. |
| Nicotinamide | | 0.1 | g. |
| Pantothenyl alcohol | | 2.00 | g. |
| Distilled water | q.s.p. | 100 | g. |
| Fresh pulp of chicken embryos | | 5 | g. |

The process is that quoted in Example 1; the fresh embryo pulp is added after cooling the emulsion, and just before the latter is distributed into cells.

EXAMPLE 20

Dentifrice paste with antibiotic

| | | |
|---|---|---|
| Lithium, sodium and magnesium triple fluosilicate | 5 | g. |
| Sodium alginate | 0.2 | g. |
| Sodium lauryl sulphate | 1 | g. |

-continued

| | | | |
|---|---|---|---|
| Sucrose | | 20 | g. |
| Sodium polymetaphosphate | | 25 | g. |
| Phosphoric acid | q.s.p.pH6 | | |
| Mint oil | | 1 | g. |
| Erythrosin | | 0.05 | g. |
| Tyrothricin | | 0.5 | g. |
| Methyl para-hydroxybenzoate | | 0.1 | g. |
| Distilled water | q.s.p. | 100 | g. |

Method of preparation

The dyestuff and the methyl para-hydroxybenzoate are dissolved in distilled water and the lithium, sodium and magnesium triple fluosilicate is allowed to swell together with these in the coloured distilled water. The pH is adjusted to 6 with phosphoric acid. The sucrose and the polymetaphosphate are added, and the whole mixed until a homogeneous fluid paste is obtained. The mint oil and the tyrothricin are emulsified in the solution obtained, and the mixture is then poured into cells of parallelepiped shape, frozen at about −35°C and lyophilised under the conditions described in Example 1.

EXAMPLE 21

Dentifrice Paste With Vaccine

The process is carried out as described in Example 20 using:

| | | | |
|---|---|---|---|
| Aluminium-magnesium double silicate | | 4 | G. |
| Hydroxyethylcellulose | | 0.25 | g. |
| Sodium lauryl sulphate | | 1 | g. |
| Sucrose | | 10 | g. |
| Sodium saccharinate | | 0.2 | g. |
| Phosphoric acid | q.s.p.pH7 | | |
| Hydrated dicalcium phosphate | | 30 | g. |
| Fresh cochineal | | 0.01 | g. |
| Fresh cochineal | | 0.01 | g. |
| Anethole | | 0.5 | g. |
| Diluted cultures of spirilla | | 2 | g. |
| Fuso-spirochetal antivirus | | 2 | g. |
| Diluted strepto-staphylococcal culture | | 2 | g. |
| Distilled water | q.s.p. | 100 | g. |

EXAMPLE 22

Dentifrice Paste With Ingredients Which Are Unstable and Incompatible in the Aqueous Phase The procedure of Example 20 is adopted, using the following ingredients:

| | | | |
|---|---|---|---|
| Lithium, magnesium and sodium triple fluosilicate | | 4. | g. |
| Polyvinylpyrrolidone | | 0.5 | g. |
| Sodium lauryl sulphate | | 1 | g. |
| Phosphoric acid | q.s.p.pH5 | | |
| Sodium polymetaphosphate | | 30 | g. |
| Mint chewing gum oil | | 1 | g. |
| Patent blue | | 0.001 | g. |
| Neoarsphenamine | | 1 | g. |
| Bacitracin | | 5,000 | I.U. |
| Sucrose | | 10 | g. |
| Sodium saccharinate | | 0.1 | g. |
| Distilled water | q.s.p. | 100 | g. |

EXAMPLE 23

Dentifrice Paste With Enzymes

The following are made into a dentifrice as described in Example 20:

| | | | |
|---|---|---|---|
| Aluminium-magnesium double silicate | | 5 | g. |
| Guar gum | | 1 | g. |
| Phosphoric acid | q.s.p.pH7 | | |

-continued

| | | |
|---|---|---|
| Sodium lauryl sulphate | 1 | g. |
| Calcium carbonate | 30 | g. |
| Sucrose | 20 | g. |
| Sodium saccharinate | 0.2 | g. |
| Lysosyme (hydrochloride) | 2 | g. |
| Papain | 0.2 | g. |
| Pancreatin | 0.2 | g. |
| Titanium dioxide | 1 | g. |
| Menthol | 0.1 | g. |
| Eugenol | 0.01 | g. |
| Vanillin | 0.005 | g. |
| Distilled water q.s.p. | 100 | g. |

EXAMPLE 24

Hair lotion containing lecithin and embryo extracts

Lipid phase

| | | |
|---|---|---|
| Palm oil sucroglyceride | 2 | g. |
| Egg lecithin | 0.5 | g. |
| Polyoxyethylenated lanolin | 5 | g. |
| Saponin | 5 | g. |

Hydrophilic phase

| | | |
|---|---|---|
| Salicylic acid | 0.5 | g. |
| Pulp of fresh chicken embryos | 5 | g. |
| Distilled water q.s.p. | 100 | g. |
| Eau de Cologne extract | 1 | g. |

The saponin and the salicylic acid are dissolved in the water heated to 70°C, and the various constituents of the lipid phase are mixed at 70°C. The lipid phase is then emulsified in the hydrophilic phase and cooled. The embryo pulp and the perfume are added, and the emulsion is either divided amongst glass or plastic bottles, or amongst cells, frozen and lyophilised under the conditions previously described.

EXAMPLE 25

Shampoo with vitamin-containing enzymes

| | | |
|---|---|---|
| Lipase | 50,000 | I.U. |
| Vitamin F | 1 | g. |
| Pantothenyl alcohol | 2 | g. |
| Vitamin B 6 | 1 | g. |
| Lavender oil | 0.1 | g. |
| Liquid Quillaya extract q.s.p. | 100 | g. |

EXAMPLE 26

Anti-dandruff Lotion With Antibiotic and Steroid

An anti-dandruff lotion is made, using the procedure described in Example 24 from the following composition:

| | | |
|---|---|---|
| Amphotericin B | 100 | mg. |
| Sodium desoxycholate | 80 | mg. |
| Disodium phosphate | 20 | mg. |
| Monosodium phosphate | 1.800 | mg. |
| Beta-methasone | 50 | mg. |
| Eau de Cologne extract | 0.1 | g. |
| Liquid Panama (bark) extract q.s.p. | 100 | g. | as indicated above, an anti-dandruff lotion is obtained.

EXAMPLE 27

Shampoo for the Treatment of Baldness

The procedure described in Example 24 is applied to the following composition:

| | | |
|---|---|---|
| Diethylstilboestrol | 1 | mg. |
| Oestrone | 0.02 | mg. |
| Cysteine | 1 | g. |
| Hexachlorophene | 0.5 | g. |
| Witchhazel extract | 10 | g. |
| Hop extract | 10 | g. |
| Liquid extract of Quillaya q.s.p. | 100 | g. |

Lyophylised products, especially those made from sludges of natural waters and from plankton, are prepared as described in Example 20 or 24.

EXAMPLE 28

Soothing Dispersion Cream Contained in a Porous Support

A cream is prepared as described in Example 1 from the following composition:

| | | |
|---|---|---|
| Cetyl alchol | 2. | g. |
| Stearyl alcohol | 2. | g. |
| Sodium lauryl sulphate | 0.5 | g. |
| Lithium, magnesium and sodium fluosilicate | 2.5 | g. |
| Pluronic F 68 (polyoxyethylene-polyoxypropanediol-1,2, marketed by Wyandotte) | 1 | g. |
| Polyethyleneglycol (molecular weight 4000) | 1 | g. |
| Carboxymethylcellulose of low viscosity | 0.15 | g. |
| Distilled water q.s.p. | 100 | g. |

Polyurethane foam having 10 to 100 pores per inch is used as the support. The foam is dipped while compressed into the fluid cream. The expansion of the compressed foam in the cream allows the cream to be absorbed. The whole is then lyophilised by the process described above. For use, the foam is rapidly steeped in water and the material is applied by rubbing over the skin.

I claim:

1. A process of preparing an emolient cream in a porous support, which comprises admixing a molten oil phase comprising a fatty alcohol and an emulsifier with a heated aqueous phase comprising an emolient, a thickener, an emulsifier and water to form an oil-in-water emulsion; cooling the emulsion to form a cream; immersing a polyurethane foam, while compressed into said cream and allowing the cream to be absorbed into the foam; and freeze-drying the foam thus impregnated with the cream.

2. A freeze-dried polyurethane foam obtained by the method of claim 1.

* * * * *